United States Patent
McNair et al.

(10) Patent No.: US 10,198,499 B1
(45) Date of Patent: Feb. 5, 2019

(54) SYNONYM DISCOVERY

(75) Inventors: Douglas S. McNair, Leawood, KS (US); Kanakasabha K. Kailasam, Olathe, KS (US); John Christopher Murrish, Overland Park, KS (US)

(73) Assignee: Cerner Innovation, Inc., Lenexa, KS (US)

( * ) Notice: Subject to any disclaimer, the term of this patent is extended or adjusted under 35 U.S.C. 154(b) by 1400 days.

(21) Appl. No.: 13/569,781

(22) Filed: Aug. 8, 2012

Related U.S. Application Data

(60) Provisional application No. 61/521,219, filed on Aug. 8, 2011.

(51) Int. Cl.
G06F 7/00 (2006.01)
G06F 17/30 (2006.01)

(52) U.S. Cl.
CPC .............................. G06F 17/30604 (2013.01)

(58) Field of Classification Search
CPC ........ G06F 19/30; G06F 19/32; G06F 19/321; G06F 19/325; G06F 19/327; G06F 19/709; G06F 19/28; G06F 17/30734; G06F 19/34; G06F 19/3406; G06F 19/3443; G06F 19/3487; G06F 19/36
USPC ................. 707/737, 754, 749, 794
See application file for complete search history.

(56) References Cited

U.S. PATENT DOCUMENTS

| | | | |
|---|---|---|---|
| 7,577,652 B1 * | 8/2009 | Rajan et al. | |
| 7,617,078 B2 * | 11/2009 | Rao | G06F 17/3061 702/181 |
| 7,844,566 B2 * | 11/2010 | Wnek | 706/55 |
| 8,015,136 B1 * | 9/2011 | Baker | G06F 19/3431 706/45 |
| 8,478,534 B2 * | 7/2013 | Zhu et al. | 702/19 |
| 8,639,446 B1 * | 1/2014 | Stupp | 702/19 |
| 8,856,156 B1 * | 10/2014 | McNair et al. | 707/756 |
| 2002/0198739 A1 * | 12/2002 | Lau | G06F 17/30604 705/3 |
| 2003/0149537 A1 * | 8/2003 | Binkowski et al. | 702/27 |
| 2005/0022168 A1 * | 1/2005 | Zhu et al. | 717/124 |
| 2005/0154708 A1 * | 7/2005 | Sun | G06F 17/30575 |
| 2005/0181350 A1 * | 8/2005 | Benja-Athon | 434/367 |
| 2006/0242140 A1 * | 10/2006 | Wnek | 707/5 |
| 2007/0269804 A1 * | 11/2007 | Liew et al. | 435/6 |
| 2008/0021288 A1 * | 1/2008 | Bowman et al. | 600/300 |
| 2008/0091471 A1 * | 4/2008 | Michon et al. | 705/3 |
| 2009/0089083 A1 * | 4/2009 | Paradis et al. | 705/2 |

(Continued)

*Primary Examiner* — Mohammed R Uddin
(74) *Attorney, Agent, or Firm* — Shook, Hardy & Bacon L.L.P

(57) ABSTRACT

Methods, systems, and computer-readable media are provided for facilitating mapping of semantically similar terms between and among two or more information systems. In particular, to facilitate automatic discovery, establishment, and/or statistical validation of linkages between a plurality of different nomenclatures employed by a plurality of information systems, such as multiple electronic health record systems. In embodiments, the imputation of latent synonymy in corpora comprised of samples of historical records from each system enables automated terminology mapping between disparate systems' records, thereby establishing reliable linkages that may subsequently be utilized for realtime decision support, data mining-based research, or other valuable purposes.

19 Claims, 5 Drawing Sheets

(56) References Cited

U.S. PATENT DOCUMENTS

| | | | |
|---|---|---|---|
| 2009/0099920 A1* | 4/2009 | Aharoni | G06Q 30/02 705/14.26 |
| 2011/0010100 A1* | 1/2011 | Li | G06F 19/18 702/19 |
| 2011/0288877 A1* | 11/2011 | Ofek et al. | 705/2 |
| 2012/0101975 A1* | 4/2012 | Khosravy | G06Q 30/02 706/55 |
| 2012/0124080 A1* | 5/2012 | Willard et al. | 707/769 |

* cited by examiner

LEARNING – JOB RESULTS

REFERENCE SYSTEM: A
TARGET SYSTEM: B
CONCEPT:   VOCABULARY: SNOMED CT
           VOCABULARY ID: 271649006
           NAME: SYSTOLIC BLOOD PRESSURE (OBSERVABLE ENTITY)

STATUS: COMPLETED
SUBMITTED AT: 2011-07-18T13:40:31.530Z
COMPLETED AT: 2011-07-18T13:41:31.706Z
THRESHOLD: 0.15

REVIEW STATUS: NOT ACCEPTED   [ACCEPT]

| | REFERENCE CODE | REFERENCE UNIT CODE | TARGET CODE | TARGET UNIT CODE | DISTANCE | RESULT COUNT |
|---|---|---|---|---|---|---|
| ☑ | CODE SET – EVENT \| SYSTOLIC BLOOD PRESSURE | N/A | CODE SET – EVENT \| SYSTOLIC BLOOD PRESSURE | N/A | 0.000 | 166 |
| ☑ | CODE SET – EVENT \| SYSTOLIC BLOOD PRESSURE | N/A | CODE SET – EVENT \| DIASTOLIC BP (SITTING) | N/A | 0.084 | 406 |
| ☑ | CODE SET – EVENT \| SYSTOLIC BLOOD PRESSURE | N/A | CODE SET – EVENT \| SYSTOLIC BP (SITTING) | N/A | 0.092 | 271 |
| ☑ | CODE SET – EVENT \| SYSTOLIC BLOOD PRESSURE | N/A | CODE SET – EVENT \| SYSTOLIC BP #1 | MMHG | 0.203 | 195 |
| ☐ | CODE SET – EVENT \| SYSTOLIC BLOOD PRESSURE | N/A | CODE SET – EVENT \| ICU SBP (SYSTOLIC BLOOD PRESSURE) | N/A | 0.210 | 500 |
| ☑ | CODE SET – EVENT \| SYSTOLIC BLOOD PRESSURE | N/A | CODE SET – EVENT \| ESTIMATED HEIGHT AT BONE AGE EXAM | CM | 0.211 | 139 |
| ☐ | CODE SET – EVENT \| SYSTOLIC BLOOD PRESSURE | N/A | CODE SET – EVENT \| SYSTOLIC BP #1 | N/A | 0.216 | 157 |
| ☐ | CODE SET – EVENT \| SYSTOLIC BLOOD PRESSURE | N/A | CODE SET – EVENT \| IAWARE_SYSTOLICCUFF | N/A | 0.219 | 478 |

*FIG. 3.*

SYNONYM DISCOVERY

CROSS REFERENCE TO RELATED APPLICATIONS

This application claims the benefit of U.S. Provisional Application No. 61/521,219, titled "SYNONYM DISCOVERY," filed Aug. 8, 2011, which is hereby expressly incorporated by reference in its entirety.

INTRODUCTION

Demands for transportable, readily-available, interoperable electronic health care records have steadily increased in recent years. Demographic changes such as an aging population with increased chronic illness and a more mobile population have created needs for larger volumes of health information that are more easily transferrable, particularly to support safe and effective longitudinal individual care regardless where the consumer may be when a medical problem arises. Furthermore, concerns about viral epidemic outbreaks and bioterrorism have focused attention on the need for a public health information infrastructure with the capability of providing aggregated population-level information on a real-time basis. The delivery of cost-effective, high quality health care in order to meet societal goals for healthy people and healthy populations is thus now clearly linked to the availability and interoperability of health information.

In November of 2001 the U.S. National Committee on Vital and Health Statistics (NCVHS) issued a report to the Secretary of Health and Human Services that called for establishing a National Health Information Infrastructure (NHII). However, the proposed U.S. National Health Information Infrastructure (NHII) did not describe a centralized database of patient information. Rather, the NHII vision is for distributed health information built on a framework within secure networks with strict confidentiality protections and a unified nomenclature coding system.

Besides the demands for accessible, geographically-distributed, interoperable information that pertains to the safe and effective longitudinal care of individuals, there are growing demands for large-scale and ongoing comparative-effectiveness research, to ascertain the relative value and effectiveness of various different modalities of medical treatments and to evaluate this in a timely manner. Traditionally, randomized controlled clinical trials have been the "gold standard" for such research. However, the rate of year-to-year change in the myriad treatments that are available for many thousands of important medical conditions is very high, and it is logistically and financially impossible for health authorities to design and fund and conduct all of the prospective randomized trials that are in principle desirable, for health policy and treatments' scientific relative value determinations to keep pace with innovations and with evolving de facto treatment practices.

In some instances, equipoise is absent and it may be unethical to conduct individually randomized prospective studies in the traditional manner. 'Equipoise' is the term used for a state of lack of evidence regarding which treatment intervention or innovation will provide the most benefit and the least harm to recipients. If in advance of commencing a study one already has evidence that Treatment A is more safe or effective than Treatment B, then equipoise is absent, and it would be unethical to expose more persons to the harms of the inferior B simply to find out quantitatively how much worse B is, or to accomplish some other objective.

In these and other circumstances, data mining and observational empirical research using case-control designs or prospective cohort research designs are solutions to the costs and limitations of traditional randomized controlled trials. But in order to conduct observational and data mining-based studies, it is necessary that the like data elements in each computer system that sources data to be analyzed be mapped or linked to like data elements in each other system. There exists a lack of the ability to reliably measure quality from unmapped electronic medical record data.

Presently, health information is typically maintained in multiple electronic health record database systems, as well as in traditional paper records, in many locations for each patient, including: physician offices, laboratories, hospitals and departments within hospitals (e.g., radiology departments), with post-acute care providers such as nursing homes and home health agencies, and, increasingly, with the consumer, in separately-managed personal health records systems.

People who have chronic health conditions and may be transferred to and from providers across the health care continuum over a period of time have a great need for interoperability of their health information that is stored within the disparate systems. Recent enactment of health reform legislation aims to improve transfer and availability and interoperability of health information through means such as 'Clinical Document Architecture' (CCD) and 'Continuity of Care Document' (CCD) standards (http://xreg2.nist.gov/cda-validation/validation.html; http://xreg2.nist.gov/cda-validation/downloads.html; http://www.hl7.org/Special/committees/structure/index.cfm). The CCD standard was originally developed by HL7 with participation from ASTM's "E31" standards committee, the technical committee responsible for development and maintenance of the 'Continuity of Care Record' (CCR) standard.

Essentially, a clinical document architecture (CDA) standard is necessary to enable the reliable algorithmic location of pertinent information within current documents, to logically organize documents in document management systems, to categorize and link information within the documents according to a defined structure, and to retrieve and display documents in electronic systems (including web-based and wireless mobile systems). While there has been considerable progress in recent years with regard to CDA and 'continuity of care document' standards, there has been little progress to achieve a unified ontology or universal nomenclature or to insure the integrity of mappings between various existing nomenclatural rubrics.

Despite the multi-year federally-sponsored efforts at standardizing the health information exchange record architecture and unifying the nomenclatures that are presently utilized within the different systems to record diagnoses, diagnostic and therapeutic procedures, pharmaceuticals, and other items, there is as yet no universally-accepted ontology or nomenclature standard for all of the domains and disciplines, and, lacking such universal standard, the organizations persist in employing the nomenclatures that they have used for many years, according to the traditions and requirements of insurance companies and payors with whom they interact, plus requirements set forth by a miscellany of state and local agencies. There is as yet no regulation or other mandate that compels the organizations to conform to one unified set of nomenclatural rubrics such that like terms assuredly refer to the same data elements across disparate computer systems, and, even were the organizations compelled to conform to some future standard yet to be promulgated, there are at this time insufficient monies and resources to implement prompt migration to a universal unified ontology.

Consequently, the absence of unified nomenclature and the financial and other impediments to creating one mean that (1) inter-systems interoperability nomenclature-linkage means to support health services statistical and observational research and policy setting and (2) inter-systems interoperability means to support real-time decision-support for the care of individual patients remain unmet needs.

Applications are under development for automated analysis of medical-related data. Techniques are being considered, for example, for receiving a triggering or new 'evoking' data item, evaluating premises of medical evidence in the context of that evoking item or event using decision-support inference engine software or artificial neural network algorithms or other means, identifying such features and classifying the features for possible diagnosis and treatment, and emitting alerts and advisory messages to the human user or undertaking action automatically. These clinical decision support (CDS) systems are becoming increasingly prevalent within individual institutions, such as hospitals. However, relatively modest inter-institutional interoperability of such programs has occurred in the past, due to the absence of interoperable or linked ontologies, and little or no activity has focused on enhancing the performance of such algorithms by novel machine-learning techniques applied across multiple venues of care, utilizing CCD or CDA information from the different information systems that are used in the various venues.

Moreover, present CDS systems are typically refined by laborious and expensive feature recognition and expert-system reprogramming by teams of programmers and technicians.

There is a need, therefore, for an improved technique that would permit efficient, affordable, interoperable refinement of statistical and epidemiologic data analysis and CDS in the multi-venue, multi-system health care context. The benefits for various stakeholders include the following:

For Consumers: (a) Realtime medical consultations and decision-support wherever the person is located; and (b) Management of one's own health care needs and their health care decision making.

For Providers: (a) Providing access to more accurate and complete real-time patient data; (b) Using clinical guidelines and protocols that reference current and historical information from disparate systems concurrently with the patient care process; (c) Preventing adverse events by providing realtime CDS actions or alerts to clinicians integrated with the patient care process workflow; and (d) Supporting continuous quality improvement processes by providing more complete and comprehensive clinical data for outcomes analysis.

For Public Health/Regulators: (a) Improving the ability to identify, monitor, and respond to health problems; (b) Accessing and reporting data needed for public health; and (c) Increasing the scope, effectiveness, timeliness, and efficiency of clinical research.

Data exploration (sometimes called "data mining") involves the development and use of tools that analyze large data sets in order to extract useful, but often hidden (or "latent") information from them. Information extracted from a particular database can be used to identify patterns of characteristics (features) and groupings (classes) of samples in the data. If the feature patterns of samples in each class are sufficiently similar within that class and are sufficiently dissimilar to the overall feature patterns of the other classes, then the feature patterns of each class may be used to develop classification rules for separating the different classes within that domain. The resulting classification rules may then be used to predict to which class a new and unclassified sample may belong based upon that new sample's feature pattern. A linkage "classifier" is the culmination of such classification rules that are generated from input data called a training set.

Conventional classification techniques typically include some kind of data exploration method that derives the classification rules. Although many classification methods already exist, they are all affected by one or more of three factors: (1) lack of interpretability, (2) assumptions made about the data when building a classifier, and (3) data requirements. The first factor is a question of how semantically interpretable the variables' provenance and modes of measurement are. In some cases, such as blood pressure monitoring, it is vital that a user be able to understand exactly what factors will allow discrimination between a blood pressure that is measured by a sphygmomanometer cuff and a blood pressure that is measured by an indwelling arterial line. In other situations, however, the distinction is of no importance and, therefore, the semantic interpretability is not as important an influence on the choice of classification method. The second factor limits the usefulness of the resulting classifier if the assumptions made when applying the classification technique are inappropriate for the given data set. The third factor affects those classification methods that require a specific size data set, or require the classes to have equivalent properties in terms of membership number or other properties such as covariance structure.

Furthermore, other attempts at addressing the synonymy discovery problems have several additional limitations, including:

(1) Labor-intensiveness, giving rise to excessive costs to develop and maintain or, conversely, giving rise to excessive false-miss Type II statistical error rates due to staleness of mappings if the mappings are not maintained on a timescale commensurate with rates of nomenclatural change in the underlying associated systems.

(2) Poor scalability, causing excessively slow response-time and/or unacceptable computer hardware expense to achieve a desired level of runtime performance. In some instances, outstripping the maximum address space in terms of physical memory and/or pagefile virtual memory.

(3) Failure to take into account the topic-scoped, context-dependent epidemiology of terms' values and the quantitative properties of statistical distributions of those values.

(4) Lack of ability to adequately reduce the dimensionality of the classification problem, such that statistical associations between terms that have large statistical explanatory power are diluted or obscured by retained 'noise' variables.

Failure types (3) and (4) result in (a) an inability to accurately and reliably establish linkages when such true linkages are latent in the underlying data, and (b) a high level of statistical uncertainty regarding the veracity and strength of such linkages, such that a very large sample size or data set is required to provide statistical power sufficient to resolve the uncertainty.

(5) Lack of practical feasibility to perform repeated regression testing and related quality-assurance procedures to determine the veracity and reliability of inter-nomenclatural linkages and mappings.

(6) Lack of ability to quickly and sensitively discover new valuable statistical associations and linkages that exist between terms that are extant in multiple disparate databases.

(7) Lack of robustness against idiosyncratic and regional variations in the use and application of terms to situations that are conceptually and semantically similar.

Accordingly, it is therefore valuable and highly desirable to provide systems, methods, and computer readable media for solving the automatic synonymy discovery problems described herein, to achieve better and more robust discovery of synonymy and quicker and more robust detection of emergent non-synonymy between two or more systems whose nomenclatures were previously satisfactorily mapped.

SUMMARY

Systems, method and computer-readable media are provided for facilitating mapping of semantically similar terms between and among two or more information systems. In particular, to facilitate automatic discovery, establishment, and/or statistical validation of linkages between a plurality of different nomenclatures employed by a plurality of information systems, such as multiple electronic health record systems. In embodiments, the imputation of latent synonymy in corpora comprised of samples of historical records from each system enables automated terminology mapping between disparate systems' records, thereby establishing reliable linkages that may subsequently be utilized for realtime decision support, data mining-based research, or other valuable purposes.

Embodiments are directed to discovery, validation, and quality assurance of nomenclatural linkages (also called 'mappings' or 'cross-walks') between pairs of terms or, alternatively, combinations of terms ('morphemes' or 'term-clusters') in databases that are extant on multiple different health information systems that do not share a set of unified codesets, nomenclatures, or ontologies to tag or code the documents and records, or that may in part rely upon unstructured free-text narrative content instead of codes or standardized tags. Embodiments of the invention discover semantic structures that exist naturally in the documents and database records maintained by those systems, including relationships of synonymy and polysemy between terms used in said documents and database records arising from disparate processes and maintained by different information systems. Some embodiments then utilize the discovered latent semantic structures to establish linkages between terms extant on the multiple systems or to validate linkages that have been established in other ways, either by manual human effort or by other algorithmic means.

In such ways, embodiments of the invention provide advantages over traditional techniques including: allowing scalable automatic discovery of synonymy and processing of mappings of nomenclatures between systems. In comparison with manual methods, automated embodiments offer advantages in terms of absolute repeatability of mappings, immunity from errors related to database coordinator fatigue, lapses of attention, and transcription, as well as efficiency and cost considerations that permit either more extensive and rigorous testing for the same cost as manual methods, or more rapid quality assurance and validation testing at lower cost.

BRIEF DESCRIPTION OF THE DRAWINGS

Embodiments of the invention are described in detail below with reference to the attached drawing figures, wherein:

FIG. 3 illustratively provide results from an embodiment; and

DETAILED DESCRIPTION

Figure 1A:
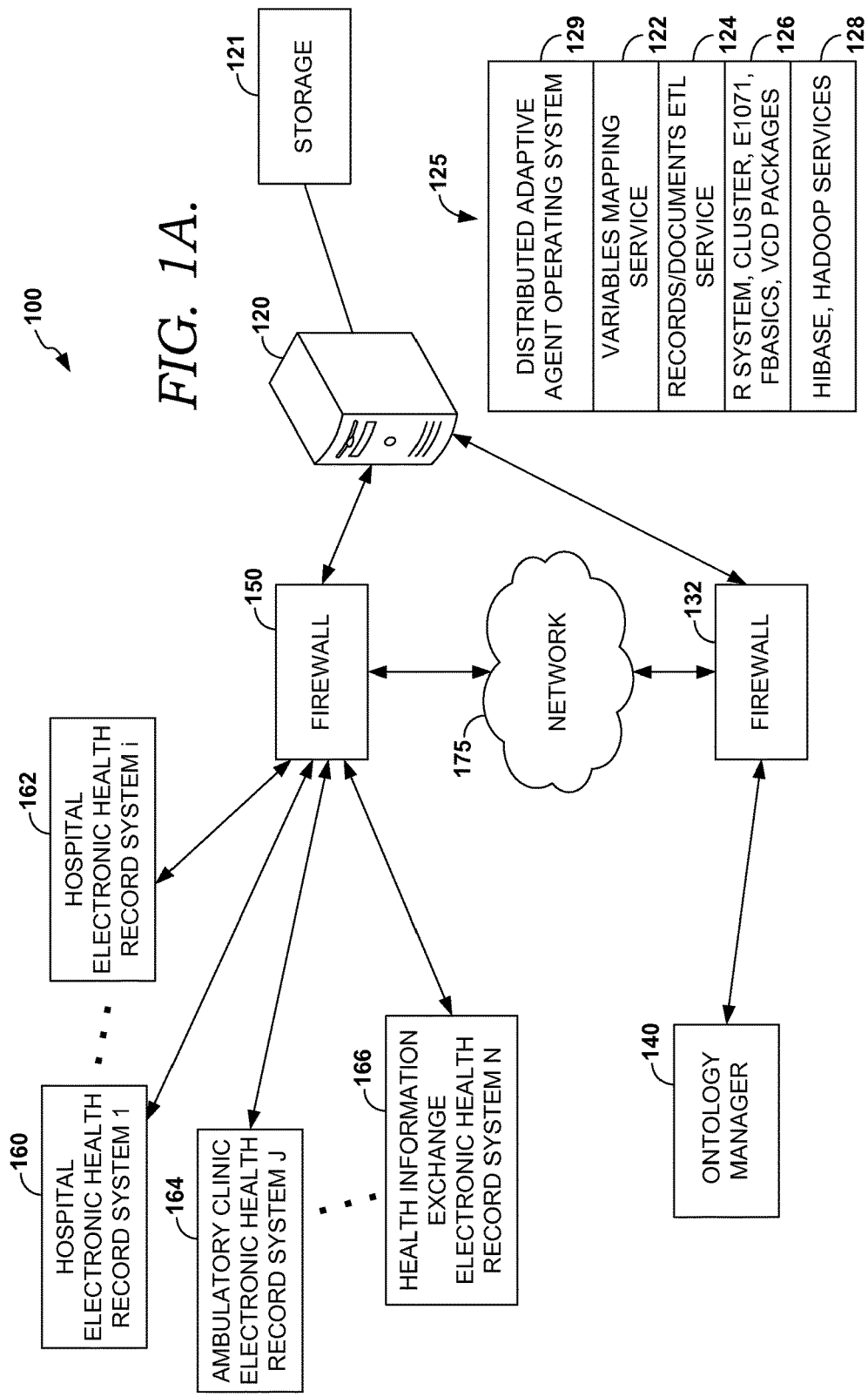
FIGS. 1A, and 1B depict aspects of an illustrative operating environment suitable for practicing embodiments of the invention.

The subject matter of the present invention is described with specificity herein to meet statutory requirements. However, the description itself is not intended to limit the scope of this patent. Rather, the inventor has contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media include both volatile and non-volatile media, removable and nonremovable media, and contemplates media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently.

As discussed above, embodiments of the invention are provided for facilitating mapping of semantically similar terms between and among two or more information systems, and in particular, automatic discovery, establishment, and/or statistical validation of linkages between a plurality of different nomenclatures employed by a plurality of information systems, such as multiple electronic health record systems.

The phrase "terminology coding systems" refers to the continuum of approaches used to assure standardized recording and encoding of clinical data in electronic record systems. Such coded data is central to the efficient exchange of information in messages sent across documents, systems and applications. Various types of terminology coding systems exist on a continuum that ranges from human readable, enumerated coding schemes to formal terminologies that enable machine "understanding."

Enumerated coding schemes emphasize encoding pre-coordinated phrases that enable users to pick the most relevant terms from pre-defined lists. Typically, such systems provide a very limited coverage of clinical content, and focus only on the specific use for which those data are required. Such systems reflect the technology available 30 years ago and the constraints that were present in relation to coding data for computer-based analysis. The MDS is an example of an enumerated coding scheme. The enormous collection of such single-purpose, stand-alone coding systems has created a situation often compared to the Tower of Babel, where different data sets and software applications are not able to meaningfully exchange or reuse data and information.

More recent research and development initiatives in electronic health records emphasize the use of formal terminologies. Formal terminology systems emphasize the indexing and retrieval of concepts and their associated terms, and the post-coordination of phrases.

Embodiments of the present invention also take advantage of statistical properties of distributions of the terms' values in such a manner that smaller sample sizes are required to establish linkages with acceptable statistical power and low false-negative error rates.

In some embodiments of the present invention, the illustrative example utilizes thresholds of D<0.14 or V<0.14 as a criterion for establishing synonymy between pairs of terms or morphemes.

Turning now to FIG. 1A there is presented in 100 an example operating environment suitable for practicing embodiments of the invention. Example operating environment 100 includes a computerized system for compiling and running an embodiment of a decision support recommendation service. With reference to FIG. 1A, a first premise electronic health record system 160 includes a network behind firewall 150 communicatively coupled to Network 175. Likewise electronic health record system i (162), electronic health records system j (164) and electronic information exchange 166 are communicatively coupled through firewall 150 to network 175. Embodiments of electronic information exchange 166 include a service provided to store and to exchange information on electronic health records systems. In embodiments, a premise electronic health records system 160 comprises separate geographical locations of interconnected, networked computers and data storage centers. A health records system 160 typically provides a customer care interface, comprising input interfaces and output interfaces for recording and displaying various data items associated with providing health care. Embodiments of electronic health record system 160 include a software application, device or sensor capable of monitoring, measuring or receiving information about a patient including one or more data items that relate to the patient's health status. In embodiments, health record system 160 is located in the patient's home, in an ambulatory setting, in an in-patient setting, or in possession of the patient. In some embodiments health records system 160 embodies a device worn by the patient, or otherwise affixed to the patient. For example, electronic health record system 160 might take the form of a software application, app, or web applet running on a computing device such as a laptop, smart phone, tablet, distributed computer system, or other computer system including a system such as that described in FIG. 1B. One example of a component of a hospital electronic record system 160 is a software application assessment form, which can be completed by a caregiver based on an input device manipulated by the caregiver, and a display system such as a speaker or a computer screen. An illustrative screenshot example of an application display screen is depicted in FIG. 3.

In Embodiments, Electronic Health Record System 160 acts as a repository of point of care health information. In some embodiments point of care health information is stored on storage system 121 which is communicatively coupled to computer system 120, and to network 175, e.g. through firewall 132. An ontology manager 140 communicates through firewall 132 to network 175. In some embodiments ontology manager 140 includes a web-based application or collection of applications that are usable to manage services provided by embodiments of the invention. In some embodiments ontology manager 140 is located or accessed on the same computer system. In some embodiments ontology manager 140 is carried out by agents on a distributed multi-agent or adaptive agent operating system as described in connection to computer system 120.

Embodiments of computer stack 125 run on a computer system such as 120 of FIG. 1A. Embodiments of software stack 125 run as a distributed system on a virtualization layer within computer system 120. In some embodiments computer system 120 includes a server cluster running an operating system such as Linux. Embodiments of software stack 125 include a distributed agent operating system 129 that can host a number of services such as 122, 124, 126, and 128. In some embodiments operating system 129 hosted services include cloud-based services. Embodiments of services 122, 124, 126, and 128 run as a local or distributed stack on a collection of personal computers and servers such as 120 and/or a computing device running manager interface 140. In some embodiments, ontology manager 140 operates in conjunction with software stack 125. In embodiments, variable mapping service 122 includes services, which may include cloud-based services for facilitating health management by patient, health care provider, or insurance provider including for example, health exchange services, health records, transactions, billing, and record keeping services, information-technology services, or other services such as those provided by Cerner Heathe™ and Healthe Intent™. Furthermore, in some embodiments operating system 129 and variable mapping service 122 provide services including cloud-based services, for persistent data storage and retrieval, adaptive agent services, and time-out detection services.

Records/Documents ETL service 124 provide services that facilitate retrieving frequent item sets, extracting database records, and cleaning the values of variables in records. In some embodiments ETL service 124 provides services that facilitate the capturing, processing, storing, analyzing and viewing of information obtained by care-provider interface 145 and related information, such as, for example, electronic medical record (EMR) information about a particular patient or set of patients, and metadata such as user settings and metrics. Software packages 126 perform statistical software operations, and include statistical calculation packages such as, in one embodiment, the open-source R system. Embodiments of services 128 include Apache Hadoop and Hbase framework that provide a distributed file system.

Exemplary variable mapping services make use of Kolmogorov-Smirnov 2-sample tests (KS2) and Cramér V test statistics using a server cluster running the Linux operating system, the open-source statistical software package R, and the R modules cluster, e1071, fBasics, and vcd. Exemplary structured discrete items are retrieved using Discern Explorer™ operating on Cerner Millennium™ systems, one of which had been mapped using Cerner's Controlled Medical Terminology (CMT™) universal concept identifier ontology.

In embodiments, Network 175 includes the Internet, a public network, or a private network. In embodiments, having firewall 150, the firewall 150 may reside on the same computing device as consumer interface 145 or may comprise a separate firewall associated with Data store 121, in some embodiments includes patient data; variables associated with recommendations; recommendation knowledge base; recommendation rules; recommendations; recommendation update statistics; operational data store, which stores events; frequent itemsets (such as "X often happens with Y", for example) and itemsets index information; association rulebases, agent libraries, and other information, patient-derived data, healthcare provider information, for example. Although depicted as a single data store, may comprise more than one data store one or multiple locations, or in the cloud. The example operating environment of FIG. 1A also includes a firewall 132 between ontology manager 140, and computer system 120.

Figure 1B:
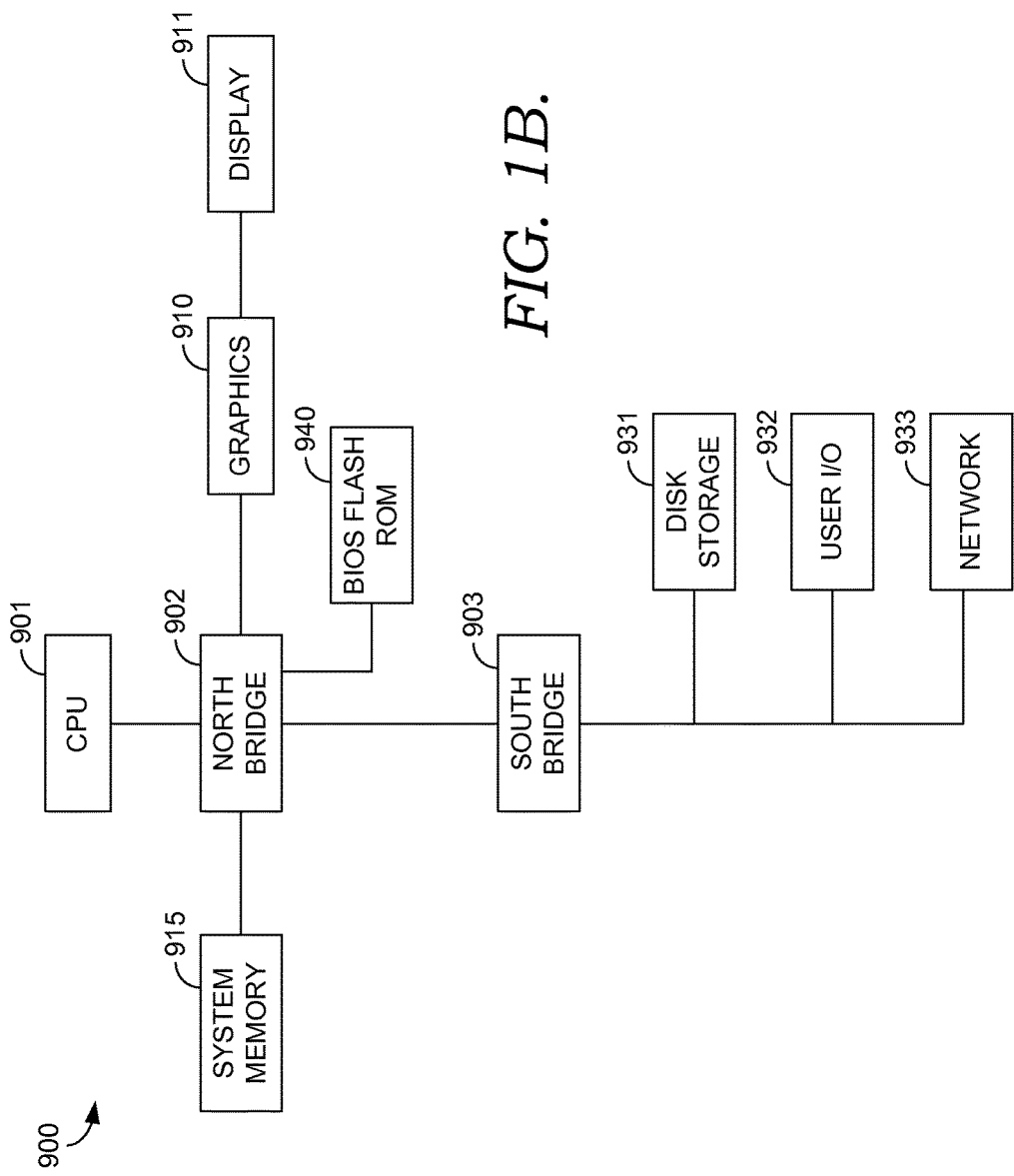

Turning now to FIG. 1B, there is shown one example of an embodiment of computer system 900 that has software instructions for storage of data and programs in computer readable media. Computer system 900 is representative of a system architecture that is suitable for computer systems such as 120. One or more CPU's such as 901 have internal memory for storage and couple to the North Bridge device 902, allowing CPU 901 to store instructions and data elements in system memory 915, or memory associated with graphics card 910 which is coupled to display 911. Bios flash ROM 940 couples to North Bridge device 902. South bridge device 903 connects to north Bridge device 902 allowing CPU 901 to store instructions and data elements in disk storage 931 such as a fixed disk or USB disk, or to make use of network 933 for remote storage. User 10 device 932 such as a communication device, a mouse, a touch screen, a joystick, a touch stick, a trackball, or keyboard, couples to CPU through South Bridge 903 as well.

In some embodiments, computing system 900 is a computing system made up of one or more computing devices. In an embodiment, computing system 900 includes an adaptive multi-agent operating system, but it will be appreciated that computing system 900 may also take the form of an adaptive single agent system or a non-agent system. Computing system 900 may be a distributed computing system, a data processing system, a centralized computing system, a single computer such as a desktop or laptop computer or a networked computing system.

In some embodiments, computing system 900 is a multi-agent computer system with agents. A multi-agent system may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control which promotes the concept of autonomy. Additional information about the capabilities and functionality of agents and distributed multi-agent operating systems, as they relate to these embodiments, is provided in U.S. patent application Ser. No. 13/250,072, filed on Sep. 30, 2011, which is herein incorporated by reference in its entirety.

Figure 2:
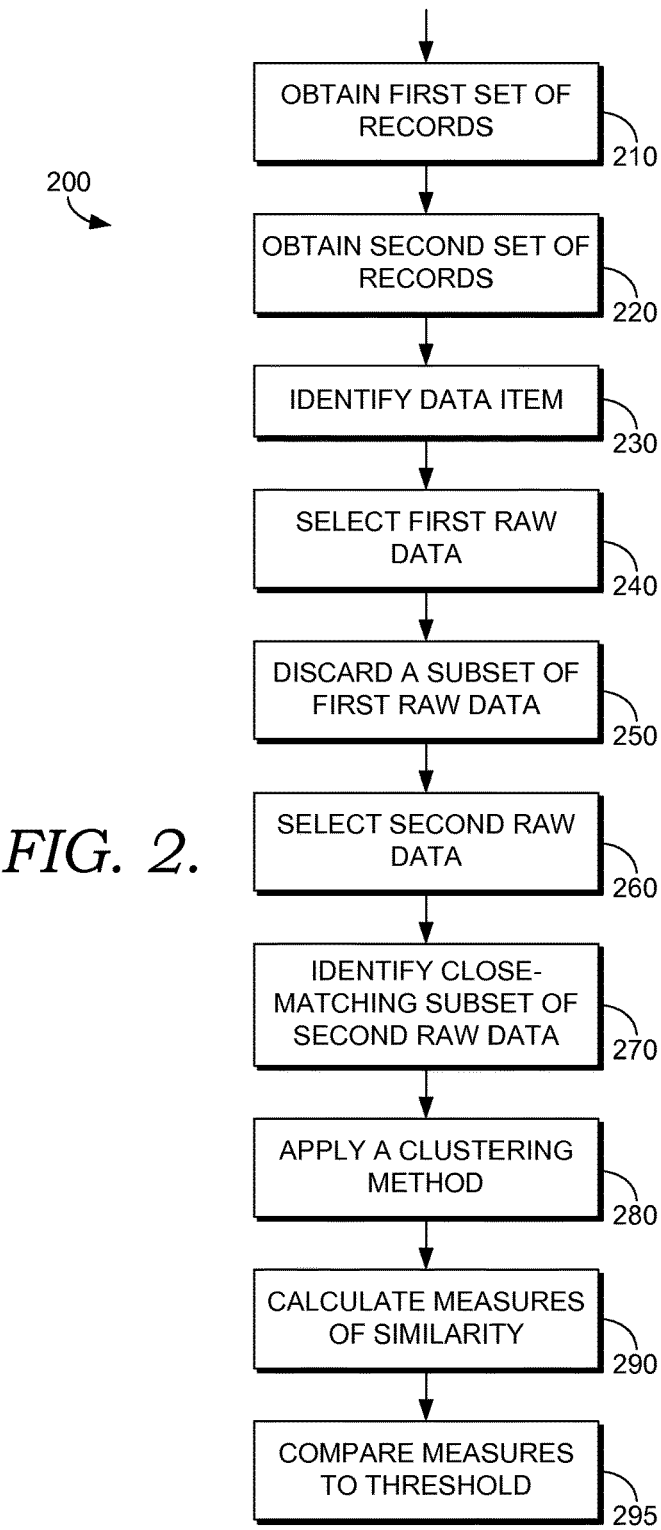
FIG. 2 depicts a flow diagram of a method for mapping of semantically similar terms between and among two or more information systems, in accordance with embodiments of the invention.

Referring to FIG. 2, a flow diagram 200 is provided for an embodiment of a method for mapping of semantically similar terms between and among two or more information systems. The flow diagram illustrates an embodiment of a system and method for generating the synonymy classifier and verifying and validating whether such a classifier achieves statistical sensitivity and specificity in the range of deployment, sufficient for satisfactory performance in the use for establishing mappings between terms in nomenclatures utilized by two or more health care information systems. At 210 a first set of data records is obtained that originates from a first health records system such as 160. In some embodiments the data is obtained locally from operating memory of a computer system such as 120. In some embodiments a computer system 120 obtains the data from network storage such as 121 or from a remote health records system 160 or from a health information exchange 166. The first set of data records represents health care information from a reference first system, let us say System A. At 220 a second set of records from a second health-records system such as heath records system 162 or 164 is obtained. The second set of health records, let us say System B, represents health record information from a second system that has an unknown correspondence or mapping. That is to say, for a selected code from system A, the corresponding codes from system B are generally unknown but desired. In some embodiments a user interface is presented to the user of an ontology manager 140 presenting visual identifiers for all available health-records systems, and an operator selects a system A as the first health records system, and selects system B as the second health records system.

At 230, one or more data items are identified to be mapped from system A to corresponding data items in system B. In an embodiment, a terminology expert associates a proprietary code in the reference system to a code from an industry acknowledged standard. An exemplary standard code has associated with it a standard description field, a standard units field, a standard value-type field, and a standard value field. Embodiments present episodes of care in a grid having each row represent data from a single instance of care, and columns that represent variables that are recorded for each episode of care. Embodiments allow an operator to click on the columns of the variables from system A that are desired to be mapped. Embodiments reflect the selection of the data items to a user by highlighting the columns to be mapped. At 240 a portion of the first raw data is selected from system A for processing by the present method. Embodiments select the data items identified at 230 in addition to ancillary demographic data associated with identified data items for each instance of care. Examples of demographic data include the patient type, reason for admission, patient height, patient weight, patient age, patient sex, units, item description, item notes, reason for care, venue type: home, clinic, emergency, outpatient, surgery, etc. Embodiments select data by forming an SQL query over available records identifying necessary data, and restricting records that are within certain ranges of demographic data so as to make the selected data homogeneous. Embodiments restrict the sex, weight, patient age, or care context so as to restrict the chosen records to a certain, chosen, homogeneous demographic subset. Embodiments adjust the restrictions to select at least 500 instances for study.

At 250 a subset of the first raw data is discarded. Embodiments apply demographic restrictions at 250. Embodiments clean the data for uniformity. Embodiments transform data values to a new interval for comparison, and discard data that does not meet quality standards. For example, if a numerical field has a textual entry, this data is discarded, or converted to a numerical value, or if data is in various units, the data is converted to standard units for comparison purposes. Examples of discarding data includes discarding extreme values from raw data, e.g. default values or obviously erroneous values. Embodiments discard 10% or less of the extreme values. Embodiments discard 5% or less on the high side, and 5% on the low side. Embodiments discard no data, so that the subset selected is the original set that was selected. Embodiments discard 5% total or 3% of the total amount of data. Embodiments discard a fraction that exceeds the mean by a weighted value that depends upon the standard deviation. For example, embodiments discard all data that is more than three standard deviations away from the mean value of the data set.

At 260 a second set of raw data is selected from data that originated from system B. Embodiments select records from the second system B that meet the same demographic restrictions that were applied in the selection of the raw data at 240. For example, if system A is a pediatric institution, with demographic attributes that identify ages 8 to 18, then the subset of system B is chosen restricted to this age range to provide a better statistical sample for comparison. Embodiments select a set of raw data from the second system B that provide at least 500 samples. Embodiments select a set of data based on an exemplary standard code and associated fields and/or an identified code and associated fields. Embodiments at 260 select the entire second data set and at 270 test the records to identify a close-matching subset of second raw data based on demographic attributes. Embodiments designate a term that is identified in the second set of raw data as a basis for cross-mapping a term to a third health-records system. Embodiments clean some data values of the subset of the second raw data by eliminating extreme values or by performing transformations on raw data to put the data in a standard form. Exemplary transformations include conversion from Celsius to Fahrenheit, etc.

At 280 a clustering method is applied to raw data from the subset of the second raw data to determine one or more clusters. Embodiments apply a cluster method to reduce the dimensionality of the raw data. Embodiments of applying a cluster method generate a decision-tree classifier. For example, a representative clustering method identifies a first cluster of numeric data and a second cluster of alphabetic data. Another representative clustering method breaks down the data values of a field to be analyzed into a spectrum of numerical values and identifies clumps of values that are relatively close to one another. An exemplary clustering method identifies clusters based on demographic attributes, e.g. breaking down by gender, race, units, description content, notes content, etc.

At 290 a quantitative similarity measure is calculated over values of the first set of data as compared to values of the second set of raw data. Embodiments make use of a non-parametric measure based on sample mean, sample standard deviation, sample median, sample absolute difference, sample difference to the mean, sample difference to the median, sample skewness, sample kurtosis, etc. Embodiments of the quantitative similarity metric operate on numerical data to compute a Kolmogorov-Smirnov 2-sample test which gives a distance D. Embodiments of the quantitative similarity metric operate on textual data by transforming the textual data by parsing the text data and tokenizing and gathering counts of encoded strings. Embodiments of the quantitative similarity metric perform the Cramer V test and make the metric equal to 1-Cramer V distance. Embodiments perform a hierarchical evaluation of potential non-parametric metrics based on sample size of the two sets and select a test based on the available sample size. For example, in embodiments, if the number of samples available is below 100, the vector of the median value and the average absolute difference to the median are used to form a vector normed distance between the two distributions; if the number of samples available is between 100 and 500 a normed distance between the vector of sample mean, sample standard deviation, and sample skewness is used; if 500 or more samples are available then the KS2 test and/or the Cramer V test are performed.

Embodiments of the quantitative similarity measure include combining a non-parametric measure of the statistical distribution of the values with a similarity measure that is based on a description in an associated field and/or combining this result with a similarity measure that is based on a units field. Embodiments combine constituent measures by adding components together. Embodiments use nCode to convert textual fields to numerical values that are used as a basis of metric calculation. Embodiments apply a distance algorithm on nCode normalized strings. Embodiments weight separate measures upon combination by weighting the value metric more heavily than the description metric and the units metric. Embodiments determine a semantic metric by calculating a similarity between a standard description field in combination with a reference description field and/or a target description field. Embodiments create the metric by using a set of weights for constituent parts that add to one. Embodiments weight the value metric by a factor of nine tenths, and the remaining metrics by a sum that adds up to one tenth. Embodiments change the weights as a function of the amount of data available. For example, if less than 500 samples are available the semantic matching term is weighted by one half, and the non-parametric value metric is weighted by one half; but if there are more than 500 samples available, then the semantic matching term is weighted by one tenth, while the non-parametric value metric is weighted by nine tenths. Embodiments form a vector of similarity metrics over a plurality of fields prior to comparison. Embodiments of a similarity metric vector include a non-parametric value similarity metric, a description similarity metric, a notes similarity metric and a units similarity metric.

At 295 a similarity metric is compared to a predetermined threshold, and if the similarity is less than the threshold, the term under consideration is provisionally bound to an identified data item as a mapping equivalent. Embodiments compare against a threshold the result of an aggregate similarity metric that is determined from a vector of weights that forms a dot product with the elements of a similarity metric vector. Embodiments perform a number of comparisons in succession and base the provisional mapping on the outcome of two or more comparisons. For example, embodiments first form a comparison based on a non-parametric value similarity metric, and if this value is below a first threshold then the term is provisionally bound in the mapping; otherwise the semantic description metric is compared to a second threshold, and if that comparison is below the second threshold, then the term is provisionally bound in the mapping, etc. In embodiments, a provisional status of synonymy is determined when the threshold is below a predetermined level. Embodiments display the provisional status in a supervisory screen such as 300 of FIG. 3. Embodiments of a concept field 370 indicate the vocabulary of the reference system, and corresponding vocabulary ID, and the data item being mapped, which in the example of supervisory screen 300 is systolic blood pressure. Embodiments display in the concept field 370 an array of data items that were mapped, and grid 351 alternately displays results found for each data item that was mapped for synonymy when alternative data items are selected by a user. Embodiments of the supervisory screen 300 are displayed on an I/O device 932 such as a monitor, LCD screen, or touch screen.

Information field 302 shows the reference system A and the target system B, as well as status, submission and completion times and an adjustable threshold currently set at 0.15. Various controls are available to globally affect the threshold used for the provisional mapping. Text box 318 allows the user to input an alternative threshold by I/O device 932 such as a keyboard, mouse, or touch screen. A slider 317 may be manipulated within slider range 319 to visually select the threshold for permitting a user to modify the threshold and so modify the items that are provisionally selected as provisionally bound to an identified data item. Additional mapping status indicators 341 and 343 also act as controls permitting a user to individually add or delete individual terms from the provisional mapping. A term is generally a textual description in a reference system identifying a coded item. In the example of FIG. 3 the target code column 310 and the reference code column 306 display terms for pairs of codes. In the example shown in FIG. 3, a check mark in control 341 indicates that row 320 of the grid 351 is provisionally mapped as equivalent to systolic blood pressure, while control 343 is un-checked indicating that the provisional mapping does not include the code set for "estimated height at bone age exam" as belonging to the provisional mapping for "systolic blood pressure."

Grid 351 displays relevant results for administrator review. Rows 320, 322, 324, 326, 328, 330, 332, and 334 indicate a term pair that can be individually selected or deselected as belonging to the mapping of terms by the corresponding control in column 304. Column 306 shows the reference code of reference system A. Column 308 displays the reference unit code in system A. Column 310 shows the target code description for comparison to the data item being reviewed. Column 312 displays the units of the target code. Column 314 indicates the distance matric for each corresponding term pair. The rows 320-334 for ease of review are presented in increasing distance metric. Column 316 shows the results count of patient records in the target system B that were used to calculate the corresponding distance of column 314. Field 365 shows the current review status of the mapping and indicates that the displayed provisional mapping has not yet been accepted by the reviewer. Embodiments present the review status as "unaccepted", "initially presented", "modified but not accepted", "accepted", "modified and accepted", etc. Representative control 360, when selected by a user through an indication of an I/O device 932 such as a mouse click updates the mapping and modifies the review status field 932 appropriately.

Embodiments of display screen 300 display partial results as they are generated. For example, row 320 is displayed as row 322 and beyond are either being computed or are queued to be computed. Embodiments compute an ordering criterion that is more readily and inexpensively computed, and that determines the order of computing the distance shown in column 314. Embodiments of an ordering criterion include the absolute difference between the sample median of the values of the two terms added to the absolute difference between the sample absolute difference to the median for the two distributions. Embodiments show the distance in column 314, re-ordering rows as the distances are computed. Embodiments choose a number of parallel agents based on a number of available machines, and display a number of partial results approximately simultaneously. For example, if there are five machines available for supporting parallel agents, row 320 is computed by machine 1 and row 330 is queued for machine 1, pending the completion of row 320. Similarly row 322 is computed by machine 2, row 324 is computed by machine 3, row 326 is computed by machine 4, and row 328 is computed by machine 5 approximately in parallel with the computation of row 320. In embodiments thousands of codes to be computed are distributed amongst machines for parallel execution of the discovery process. Embodiments order 5 results at a time into the list of already displayed items. Embodiments allow a user to review 5 results at a time by selecting button 360, and thus advancing through the list of potential matches.

Approximately 935,000 result values for fifty-seven thousand subjects cared for by one hospital were compared to a comparable number of values of vital signs and laboratory values from a reference facility whose items had previously been manually matched by human nomenclature curators. Application of an embodiment of the invention in this instance was able to correctly resolve 100% of the true synonymous term mappings between the two systems and exhibited less than 35% false-positive and 0% false-negative proposed synonym classifications.

Matching was successful using the daisy algorithm with Gower or Manhattan distance measures to select the best matched control record for each case record. In the illustrative embodiment, a 1:1 ratio is established between the cases and controls. In general, sample sizes not less than 500 cases and 500 controls, or more preferably between 1,000 and 10,000 of each, are required to establish synonymy with >99% sensitivity and >99.9% specificity.

High sensitivity is required in order to achieve the valuable objective of automatic synonymy discovery. A negative result for a threshold test that has high sensitivity is able to accurately rule-out synonymy and achieve low Type II statistical error and a low false-negative rate.

In typical target systems and reference systems, each of which has many tens of thousands of item categories to be mapped, the prevalence of intersystems synonymy for pairs of target and reference system terms is very small, frequently less than 1 in 10,000. As such, the specificity of a synonymy discovery method is the most important performance criterion. A positive result for a threshold test that has very high specificity is able to accurately rule-in synonymy and achieve low Type I statistical error and an acceptably low false-positive rate, despite the low prevalence of intersystems synonymy.

With fewer than 500 cases and fewer than 500 matched controls, the false-negative rate for KS2 and Cramér V methods may exceed 1%. Such a result would necessitate labor-intensive intervention to detect and validate the true mappings that were missed, which it is an object of embodiments of the present invention to avoid. Therefore, it is preferable for the distributions compared to each consist of a sample of 1,000 or more records.

Figure 4:
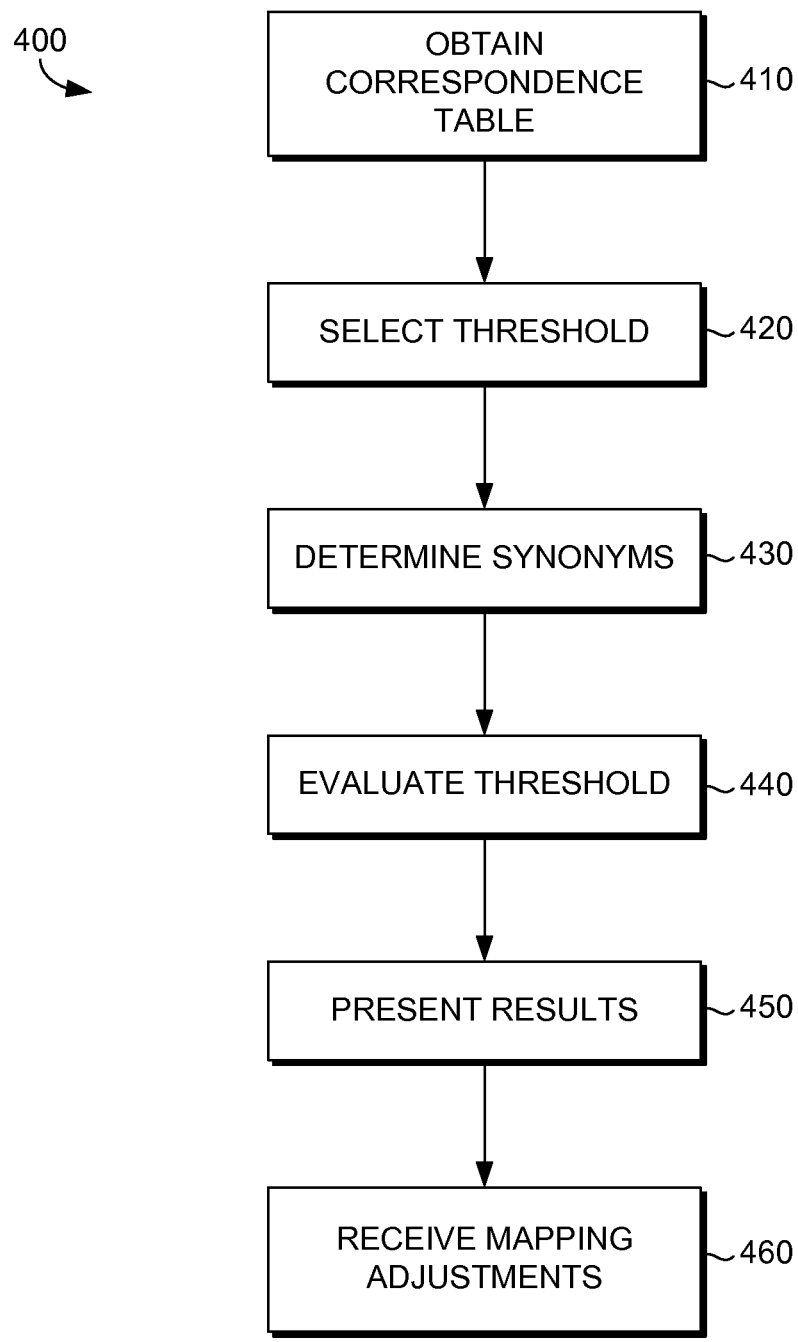
FIG. 4 depicts a flow diagram of validating latent relationships in data, illustrating embodiments of threshold selection.

Turning now to FIG. 4, there is depicted in 400 a representative flow diagram for illustrating a computerized method for validating a synonym mapping system illustrating threshold selection. At 410 a correspondence table is obtained that gives a set of terms from a target data set B that are "correctly" mapped from a reference data set A. Embodiments of the correspondence table are obtained by employing a human auditor to manually review some records from target system B and to identify some fields as correctly corresponding to a selected data item. Embodiments of obtaining a correspondence table use the hold-out method to exclude some of the records from the reference data set, and to attribute these records as belonging to a phantom target system B. In this way, the true mapping is known, because the target system is drawn from the reference system itself. Embodiments of the hold out method randomly assign half of the records of reference system A to reference system B. Embodiments assign a subset of the reference system A to a phantom system B, that are statistically roughly equivalent to a third target system C that is desired to be mapped. For example, suppose that system C has an average of only 250 instances per potential term available with the demographic restrictions selected. At 410 embodiments hold out 250 samples for each term that fit the demographic restrictions, and this is used as a phantom set B for purposes of threshold selection and validation.

At 420 a threshold is selected. Embodiments provide a default threshold which is an average of previous thresholds that have been finally selected for prior exemplary mappings. Embodiments keep a separate threshold associated with each reference term that has been successfully mapped in the past. Embodiments set a default threshold such as 0.25 which is a programmed constant adjusted so as to minimize time spent performing the validation algorithm. At 430 the synonyms are determined for the reference system A and for the target system B. Embodiments of 430 determine the synonyms based on the provisional mapping as defined in method 200.

At 440 the threshold used is evaluated. Embodiments sort the potential thresholds that might be used to give at least one additional term per adjusted threshold. For example, using the returns of FIG. 3, a threshold delta of 0.0005 is added to each distance. Embodiments determine the threshold delta from the gaps between adjacent distances, choosing the delta to be smaller than the smallest positive gap between adjacent distances. A first threshold of 0.0005 is used, and a first vector of type I and type II errors for the mapping threshold is determined. Next a threshold of 0.0845 is used and a second vector of type I and type II errors for the mapping threshold is determined. Next a threshold of 0.0925 is used and a third vector of type I and type II errors for the mapping threshold is determined. The method proceeds similarly until a user-defined criterion, such as a maximum distance is achieved, or a maximum number of false positives occurs, or a minimum number of false negatives occurs. Embodiments determine the threshold to be that which provides minimum error. Embodiments determine the threshold based on the threshold that gives zero false negatives. Embodiments increase the default threshold by a fraction of the final threshold to allow for sample variation. Embodiments increase the default threshold by 25% of the determined value. Embodiments increase the default threshold to give no more than a certain number of additional data items for review in the validation set.

At 450 results of the provisional mapping are presented to the user using a display screen like that shown in FIG. 3. Embodiments display in field 318 the threshold that was determined automatically based on the method performed. At 460 mapping adjustments are received by receiving an alternative threshold in text box 318, or by user manipulation of slider 317. Embodiments receive mapping adjustments at 460 when the user selects the accept button 360 after modifying the threshold displayed. Embodiments store the threshold for an individual data item such as systolic blood pressure. Embodiments store the threshold globally for a set of data items related to a selected thresholds.

Below is a table showing an example of Synonym Discoverer for systolic blood pressure where a sensitivity of 100% was achieved, a specificity of 99.98% and a synonym prevalence of 0.04%:

| Threshold | True Synonym pairs | Non-Synonym Pairs |
|---|---|---|
| KS2 D < 0.14 | 8 | 4 |
| KS2D ≥ 0.14 | 0 | 19818 |

Additionally, in some embodiments natural language processing (e.g., nCode) may be performed to determine the variables. In some embodiments, this language processing may be facilitated by an agent such as an agent operating on a multi-agent distributed computing system. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control which promotes the concept of autonomy. For example, in one embodiment, data may be received in the form of a natural-language narrative, such as a physicians note, and a data-extraction agent, such as a natural-language processing agent, may be invoked, to extract discrete variables from the note.

In an embodiment, a data processing system and analysis method for discovering and validating latent relationships in data. In an embodiment the method comprises obtaining or extracting the records and/or documents (corpora) from a plurality of source record-keeping systems or computer databases. In an embodiment the method comprises selecting the raw data for a plurality of variables, together with demographic attributes associated with the cases from the episodes of care that were associated with each data item, from a target source system whose item nomenclatures may or may not have been previously mapped. In an embodiment the method comprises discarding extremal (outlier) values, comprising not more than 10% of the raw data selected. In an embodiment the method comprises, for the variable that is to be newly mapped or whose previous mapping is to be validation-tested, selecting a larger quantity of raw data, together with demographic attributes for the episodes of care that gave rise to each data item, from a previously mapped reference system. In an embodiment, the method comprises applying a cluster-finding algorithm, taking each data item from the target source dataset and identifying one or more close matches from the reference dataset, matching on a plurality of demographic variables that are present in both the target system and the reference system. In an embodiment the method comprises optionally, designating the reference system as a 'gold-standard', whose nomenclatures will be used as a basis for cross-mapping terms from each of the other systems. In an embodiment, the method comprises cleaning and, if necessary, mathematically transforming the records' variables' values. In an embodiment the method comprises reducing the dimensionality by decision-tree classifier generation for the endpoint(s) or by applying other statistical clustering methods. In an embodiment the method comprises calculating quantitative measures of similarity for each of the relevant pairs of variables emanating from the different systems, using two-sample Kolmogorov-Smirnov D or Cramér V or other suitable similarity metric. In an embodiment, the method comprises comparing the measures from the previous Step to a threshold value that has been empirically established as denoting synonymy in the context of the selected use-case or topic, for the purpose of binding provisional mappings of the variables, in each of the computer systems in which linkages are sought.

In an embodiment the method uses threshold comparisons to establish synonymy relationships by measuring statistical distributions' degree of dissimilarity from each other, between semantically synonymous or nearly-synonymous terms in the corpora arising from disparate processes in different record-keeping systems or computer databases. In an embodiment the method uses one or more quantitative distance measures to establish adequate similarity between the cases from the target system and the controls from the reference system, to insure that the threshold comparisons recited in claim 2 do not result in an excessive rate of false-positive declarations of synonymy nor an excessive false-negative rate of declaring nonsynonymy between terms in the target system and the selected term in the reference system.

Many different arrangements of the various components and steps depicted, as well as components and steps not shown, are possible without departing from the spirit and scope of the invention. Embodiments of the invention have been described with the intent to be illustrative rather than restrictive. Alternate embodiments will become apparent to those skilled in the art that do not depart form its scope. A skilled artisan may develop alternative means for implementing the aforementioned improvements without departing from the scope of the present invention.

Although embodiments of the invention have been described with reference to the illustrative embodiments in the accompanying drawings, it would be understood by one skilled in the art that substitutions may be made and equivalents employed herein without departing from the scope of the embodiments of the invention as claimed. For example, additional steps may be added and steps omitted without departing from the scope.

Although the invention has been described with reference to the embodiments illustrated in the attached drawing figures, it is noted that substitutions may be made and equivalents employed herein without departing from the scope of the invention as recited in the claims. For example, additional steps may be added and steps omitted without departing from the scope of the invention.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention. For example embodiments of the invention may be used It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the claims.

What is claimed is:

1. One or more non-transitory computer-readable media having computer-usable instructions embodied thereon that, when executed, enable a processor to perform a method of discovering latent relationships in data, said method comprising:
   obtaining a first set of records from a first health-records system, the first health-records system having a first structure corresponding to the organization of the first set of records and comprising a set of unified codesets, nomenclature rubric, or unified ontology;
   obtaining a second set of records from a second health-records system, the second health-records system having a second structure corresponding to the organization of the second set of records and comprising a set of unified codesets, nomenclature rubric, or unified ontology, based on one or more terms, the first structure being incompatible with the second structure;
   identifying at least one data item associated with episodes of care within said first set of records;
   selecting first raw data from the first set of records comprising a plurality of instances associated with the at least one data item, the first raw data comprising a set of values associated with the at least one data item;
   discarding extreme values of said first raw data;
   selecting second raw data from the second set of records, the second raw data comprising a set of values;
   determining a subset of the second raw data records as closely matching the at least one data item, the identifying for each of the at least one data item comprising:
   generating one or more clusters by applying a clustering method to the subset of the second raw data;
   calculating at least one measure quantifying similarity between the at least one cluster and the first raw data; and
   determining the subset of the second raw data as closely matching the data item in response to the at least one measure quantifying similarity being less than a predetermined threshold; and
   in response to determining that the subset of the second raw data records closely match the at least one data item, creating a provisional binding of at least one of the one or more terms associated with the at least one cluster in the second health record system to the data item in the first health-records system, thereby generating, at least partially, a mapping of the first structure to the second structure.

2. The non-transitory computer-readable media of claim 1, wherein the selecting first raw data from the first set of records comprises selecting records containing demographic attributes associated with episodes of care that are associated with the data item.

3. The non-transitory computer-readable media of claim 2, wherein the selecting second raw data from the second set of records comprises matching one or more demographic attributes associated with the first set of records to demographic attributes from the second set of records.

4. The non-transitory computer-readable media of claim 1, further comprising: using a term identified by mapped clusters as a basis for cross-mapping the term to a third health-records system.

5. The non-transitory computer-readable media of claim 1, wherein the calculating at least one measure quantifying similarity comprises using a two-sample Kolmogorov-Smirnov D test.

6. The non-transitory computer-readable media of claim 1, wherein the calculating at least one measure quantifying similarity comprises using a non-parametric metric.

7. The non-transitory computer-readable media of claim 6, wherein the calculating at least one measure quantifying similarity comprises using a Cramer V test.

8. The non-transitory computer-readable media of claim 1, wherein the applying a cluster method involves reducing the dimensionality.

9. The non-transitory computer-readable media of claim 1, wherein the applying a cluster method comprises generating a decision-tree classifier.

10. The non-transitory computer-readable media of claim 1, further comprising displaying a supervisory screen presenting the provisional binding, thereby permitting a user to modify the mapping by including or excluding terms from the provisional mapping.

11. The non-transitory computer-readable media of claim 1, wherein the identifying a subset of said second raw data records as closely matching the data item comprises matching a plurality of data values within the first raw data and the second raw data.

12. The non-transitory computer-readable media of claim 1, further comprising reducing said subset of said second raw data records by cleaning the subset of extreme values.

13. The non-transitory computer-readable media of claim 12, further comprising transforming some values of the subset of the second raw data.

14. A method for discovering latent relationships in data, the method comprising:
  obtaining a first set of records from a first health-records system, the first health-records system having a first structure corresponding to the organization of the first set of records and comprising a set of unified codesets, nomenclature rubric, or unified ontology;
  obtaining a second set of records from a second health-records system, the second health-records system having a second structure corresponding to the organization of the second set of records and comprising a set of unified codesets, nomenclature rubric, or unified ontology, based on one or more terms, the first structure being incompatible with the second structure;
  identifying at least one data item associated with episodes of care within said first set of records;
  selecting first raw data from the first set of records comprising a plurality of instances associated with the at least one data item, the first raw data comprising a set of values associated with the at least one data item;
  discarding extreme values of said first raw data;
  selecting second raw data from the second set of records, the second raw data comprising a set of values;
  determining a subset of the second raw data records as closely matching the at least one data item, the identifying for each of the at least one data item comprising:
  generating one or more clusters by applying a clustering method to the subset of the second raw data;
  calculating at least one measure quantifying similarity between the at least one cluster and the first raw data; and
  determining the subset of the second raw data as closely matching the data item in response to comparing the measure quantifying similarity being less than a predetermined threshold; and
  in response to determining that the subset of the second raw data records closely match the at least one data item, creating a provisional binding of at least one of the one or more terms associated with the at least one cluster in the second health record system to the data item in the first health-records system thereby generating, at least partially, a mapping of the first structure to the second structure.

15. The method of claim 14, further comprising displaying a supervisory screen presenting the provisional binding, thereby permitting a user to modify the mapping by including or excluding clusters from the provisional mapping.

16. The method of claim 15, wherein said measure is a non-parametric measure.

17. The method of claim 16, wherein said non-parametric measure uses a two-sample Kolmogorov-Smirnov D test.

18. The method of claim 16, wherein said non-parametric measure uses a Cramer V test.

19. The method of claim 16, wherein the selecting first raw data from the first set of records comprises selecting records containing demographic attributes associated with episodes of care that are associated with the data item, and wherein the selecting second raw data from the second set of records comprises matching one or more demographic attributes associated with the first set of records to demographic attributes from the second set of records.

* * * * *

UNITED STATES PATENT AND TRADEMARK OFFICE
CERTIFICATE OF CORRECTION

PATENT NO. : 10,198,499 B1
APPLICATION NO. : 13/569781
DATED : February 5, 2019
INVENTOR(S) : Douglas S. McNair et al.

It is certified that error appears in the above-identified patent and that said Letters Patent is hereby corrected as shown below:

In the Specification

Column 08, Line 45: Please remove "HeatheTM" and replace with --HealtheTM--.

Column 09, Line 13: Please remove "firewall associated with" and replace with --firewall.--.

Column 10, Line 28: Please remove "heath" and replace with --health--.

Column 17, Line 33: Please remove "form" and replace with --from--.

Column 17, Lines 61-62: Please remove "For example embodiments of the invention may be used".

Signed and Sealed this
Twenty-sixth Day of March, 2019

Andrei Iancu
*Director of the United States Patent and Trademark Office*